US009775564B2

(12) United States Patent
Parks et al.

(10) Patent No.: US 9,775,564 B2
(45) Date of Patent: Oct. 3, 2017

(54) ANAL FIXATION DEVICE

(71) Applicants: GIVEN IMAGING LTD., Yoqneam (IL); MAYO FOUNDATION FOR MEDICAL EDUCATION AND RESEARCH, Rochester, MN (US)

(72) Inventors: Thomas R. Parks, Mammoth Lakes, CA (US); Sanket Khandelwal, Culver City, CA (US); Adil E. Bharucha, Rochester, MN (US)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

(21) Appl. No.: 14/438,791

(22) PCT Filed: Oct. 29, 2013

(86) PCT No.: PCT/IL2013/050884
§ 371 (c)(1),
(2) Date: Apr. 27, 2015

(87) PCT Pub. No.: WO2014/068560
PCT Pub. Date: May 8, 2014

(65) Prior Publication Data
US 2015/0257703 A1 Sep. 17, 2015

Related U.S. Application Data

(60) Provisional application No. 61/720,881, filed on Oct. 31, 2012.

(51) Int. Cl.
*A61B 1/32* (2006.01)
*A61B 5/00* (2006.01)
(Continued)

(52) U.S. Cl.
CPC .......... *A61B 5/6852* (2013.01); *A61B 5/1107* (2013.01); *A61B 5/4255* (2013.01);
(Continued)

(58) Field of Classification Search
CPC .. A61B 1/31; A61B 1/32; A61B 17/02; A61B 17/0206; A61B 17/0212; A61B 2017/345; A61B 2017/3452; A61M 29/00
(Continued)

(56) References Cited

U.S. PATENT DOCUMENTS 1,094,575 A * 4/1914 Joutras ............... A61B 17/0206
600/219
1,547,127 A 7/1925 Metzger
(Continued)

FOREIGN PATENT DOCUMENTS

WO WO 2007/131109 A2 11/2007

OTHER PUBLICATIONS

Supplementary European Search Report for European Application No. 13 85 1116, dated Sep. 15, 2015.
(Continued)

*Primary Examiner* — Eduardo C Robert
*Assistant Examiner* — Michelle C Eckman
(74) *Attorney, Agent, or Firm* — Pearl Cohen Zedek Latzer Baratz LLP

(57) ABSTRACT

Anorectal diagnostic procedures are oftentimes carried out with the patient laying in the left decubitus position, which leads to non-representative response to test maneuvers due to the unnatural position and patient anxiety. Devices spanning, or fastened on, the interglutial cleft of a patient allow for a more natural patient position and eliminate non-representative responses.

22 Claims, 5 Drawing Sheets

(51) Int. Cl.
*A61F 5/00* (2006.01)
*A61M 25/02* (2006.01)
*A61B 5/11* (2006.01)

(52) U.S. Cl.
CPC ........... *A61F 5/0093* (2013.01); *A61M 25/02* (2013.01); *A61B 5/6879* (2013.01); *A61M 2025/024* (2013.01); *A61M 2025/028* (2013.01); *A61M 2025/0213* (2013.01); *A61M 2025/0266* (2013.01)

(58) Field of Classification Search
USPC ................ 600/204, 206, 208, 218, 220–221, 600/235–243
See application file for complete search history.

(56) References Cited

U.S. PATENT DOCUMENTS

| | | | | |
|---|---|---|---|---|
| 2,238,563 | A * | 4/1941 | Jacques | A61B 17/02 27/21.1 |
| 3,765,401 | A | 10/1973 | Vass | |
| 3,826,242 | A | 7/1974 | Eggers | |
| 3,946,742 | A * | 3/1976 | Eross | A61M 16/0488 128/207.17 |
| 4,240,436 | A | 12/1980 | Singleton | |
| 4,365,631 | A | 12/1982 | Kline | |
| 5,433,190 | A * | 7/1995 | Sunalp | A61B 17/0231 600/236 |
| 5,470,321 | A * | 11/1995 | Forster | A61M 25/02 128/DIG. 26 |
| 6,096,057 | A | 8/2000 | Klingenstein | |
| 6,322,500 | B1 * | 11/2001 | Sikora | A61B 17/0206 600/219 |
| 6,716,229 | B2 | 4/2004 | Toth | |
| 7,766,931 | B2 | 8/2010 | Blurton | |
| 7,944,008 | B2 | 5/2011 | Parks et al. | |
| 8,597,181 | B1 * | 12/2013 | Sasaki | A61B 1/32 600/201 |
| 2005/0252514 | A1 * | 11/2005 | Taljaard | A61M 16/0488 128/207.14 |
| 2006/0063979 | A1 * | 3/2006 | Rosenblood | A61B 1/0669 600/237 |
| 2007/0031466 | A1 | 2/2007 | Blurton | |
| 2008/0096165 | A1 * | 4/2008 | Virnicchi | A61B 1/00096 433/140 |
| 2009/0167848 | A1 * | 7/2009 | Eren | A61B 1/24 348/66 |
| 2011/0060194 | A1 * | 3/2011 | Risto | A61B 1/32 600/210 |
| 2012/0215135 | A1 | 8/2012 | Galliano et al. | |
| 2013/0046328 | A1 | 2/2013 | Bourque | |

OTHER PUBLICATIONS

International Search Report for PCT International Application No. PCT/IL2013/050884, mailed Feb. 7, 2014.

* cited by examiner

STEP 1.
HOLD THE AR FIXATION
DEVICE BY THE CATHETER
FASTENING ARM

STEP 2.
INSERT THE CATHETER AS
APPROPRIATE

STEP 3.
PULL THE ELASTIC BAND

STEP 4.
ANCHOR THE BAND TO THE
'DOME'

ANAL FIXATION DEVICE

CROSS-REFERENCE TO RELATED APPLICATIONS

This application is a National Phase Application of PCT International Application No. PCT/IL2013/050884, International Filing Date Oct. 29, 2013, claiming priority of U.S. Patent Application No. 61/720,881, filed Oct. 31, 2012, which is hereby incorporated by reference.

FIELD OF THE INVENTION

The present invention relates to device and assemblies for affixing a catheter to be used in both conventional and high-resolution anorectal manometry ("ARM") and mano-defecography.

BACKGROUND OF THE INVENTION

A host of diseases or disorders, such as, for example, Hirschsprung's disease and, anismus (also known as spastic pelvic floor syndrome, anal sphincter dyssynergia, pelvic floor dyssynergia, dyssynergic defecation and paradoxal puborectal contraction) may cause difficult or uncontrollable defecation. Diagnostic techniques for identifying these, and similar, disorders may involve a simple physical examination by a trained professional. Oftentimes, however, a more invasive and involved process is required.

For example, procedures such as anorectal manometry, conventional and high-resolution anorectal manometry (ARM) or mano-defecography may be used to evaluate the functioning of the anal canal. These techniques may be performed by inserting a probe into the anal canal and measuring the pressure exerted by the sphincter muscles that ring the canal. Anal pressure that is higher than normal may be related to constipation, while anal pressure that is too low may cause fecal incontinence. Additionally, abnormal reflexes in the rectum may signal certain congenital or infectious diseases associated with constipation. Measurements made by the probes at different points in the rectum and anal canal may help locate any problem in the functioning of the anorectal muscles or nerves.

Appropriate probes for use with these techniques are known in the prior art and include, for example, Sierra Scientific Instruments' ManoScan™ anorectal catheters and probes, as well as the probes described in, for example, U.S. Pat. No. 7,944,008, entitled SUSPENDED MEMBRANE PRESSURE SENSING ARRAY.

Current practice of the above techniques often requires two or more technicians: one technician to operate the electronic workstation for the collection of data, and another technician to hold the probe in place during the procedure. Other activities of the procedure may be done by a technician, including insertion of the probe, inflation of an intrarectal balloon, which is part of the catheter assembly, training the patient to perform specific maneuvers, and removal of the probe after data are collected.

Currently, most of the procedures are performed while the patient is in the left lateral decubitus position (i.e., lying laterally on the left side). However, this position does not represent normal daytime activity and is especially not representative of a normal body position during defecation. Performing the procedures in this unnatural position may lead to non-representative (unreliable) responses to specific test maneuvers, such as, for example, "Bear Down" or "Attempted Defecation" maneuvers, because of the unnatural posture and perhaps because of patient self-consciousness about the possibility of soiling the examination environment (e.g., an examination table).

As such, there is a need in the art to eliminate non-representative responses to test maneuvers and to allow for more natural patient positions other than the left lateral decubitus position, and reduce the need for technician involvement, including the possibility of reducing the number of required technicians to one.

SUMMARY OF THE INVENTION

Accordingly, it is an object of the present invention to provide an apparatus that allows for a more natural patient position (e.g., sitting upright and the ability to sit on a commode) and thereby providing more diagnostically representative/reliable test results. By use of the device assemblies of the present invention in conjunction with a toilet or toilet-like device, the patient may assume or be in a natural sitting position and be free of anxiety over making a mess during attempted defecation maneuvers.

Additionally, it is an object of the present invention to reduce operator workload and possibly eliminate the need for a second technician during anorectal manometry, high-resolution manometry or mano-defecography procedures.

It is a further object of the present invention to reduce or eliminate measurement artifacts due to movement of the probe during the procedure. For example, when the probe is held by hand, the probe may move in response to internal pressure changes in the patient and muscular activity in the sphincter and other muscles. This kind of movement can cause errors in measurement. For example, a sensor that is initially placed in the high pressure zone of the sphincter may move distally and out of the high-pressure zone during a "Bear Down" maneuver. However, it is noted that this distal movement is less of a concern when high-resolution manometry (HRM) is employed, since the high axial density of sensors assures that at least one sensor will always be near or at the high-pressure zone.

It is a further object of the present invention to maintain the probe near or over the center of the anal canal in order to reduce measurement artifacts due to side pressure produced by holding the probe by hand.

It is also an object of the present invention to provide a large central open space for passage of stools during "Bear Down" maneuvers. A large central open space for passage of stools may lead to less patient anxiety and self-consciousness because the patient is less worried about "making a mess".

It is a further object of the present invention to accommodate opening and narrowing differences in the region of the perineum and interglutial cleft due to varying patient morphology and to motion of a patient during the procedure.

An anal affixation device for use in anorectal diagnostic procedures may include a housing for spanning the interglutial cleft of a subject. The housing may be configured to accept/hold a probe and to maintain the probe in a fixed position relative to the subject's body (e.g., subject's anus verge) during an anorectal diagnostic procedure. The housing may be configured to span the interglutial cleft of a subject in order to facilitate insertion of the probe through the anus and performance of the anorectal diagnostic procedure. The housing may take the form of, for example, a bracket, a wedge or a flexible leaf spring assembly, as described below, or a device/apparatus resembling them. Aspects of the present invention include a device assembly for use in anorectal diagnostic procedures, wherein the device assembly comprises a housing configured to accept a probe, wherein the housing can span the interglutial cleft of a patient (e.g., by being inserted into interglutial cleft, or otherwise) and allows for a natural sitting position during the procedure. In certain embodiments of the present invention, the housing of the device assembly comprises a bracket. The width of the bracket may be configured to allow the bracket to rest between the patient's buttocks and a commode seat. In certain embodiments of the present invention, the housing of the device assembly comprises a central hole for accepting the probe. In certain embodiments of the present invention, the housing is manufactured from a plastic material.

Aspects of the present invention include a device assembly for use in anorectal diagnostic procedures, wherein the device assembly comprises a housing configured to accept a probe, wherein the housing is fastened at, or adjacent to, the interglutial cleft of a patient and allows for a natural sitting position during the procedure. In certain embodiments of the present invention, the housing of the device assembly has a half wedge shape, while in other embodiments the housing has a full wedge shape. In certain embodiments of the present invention, the full wedge shaped housing further comprises a central tube or opening for accepting the probe. In certain embodiments of the present invention, the housing of the device assembly is manufactured from a soft foam material and/or flexible material.

Aspects of the present invention include a device assembly for use in anorectal diagnostic procedures, wherein the device assembly comprises a housing comprising two arms configured in a two-sided leaf spring shape, and a probe support arm fixed to the housing. The probe support arm may be connected to the housing, extend in-between the two arms and configured to accept the probe for performing an anorectal diagnostic procedure. In certain embodiments of the present invention, the housing of the device assembly is manufactured from a semi-rigid plastic. In other embodiments, the housing may be or include a flexible material (e.g., teslin) or have lengthwise gradual flexibility, which may more readily conform to (e.g., better suits) the configuration of the gluteal area, while preserving durability.

In certain embodiments of the present invention, the housing further comprises a soft foam material. The foam material may be arranged as, or form, foam strips configured on the exterior portions of the two arms of the housing, although the soft foam material may be placed anywhere on the device as needed. The foam material may further comprise an adhesive material for fastening the housing to the patient. In certain embodiments of the present invention, the probe support arm of the housing may extend and be fixed in-between the two arms ('wings') of the housing.

In certain embodiments of the present invention, the probe support arm further comprises a means for fastening the anorectal probe to the probe support arm. A person having ordinary skill in the art will appreciate that there are many ways of fastening the probe to the probe support arm, such as, for example, a belt-like elastic band, a clamp-like structure, a tapered lock piece, or a stopper. The present invention can be configured in different sizes in order to approximate to, or accommodate for, differences in configuration of the human body and gluteal area among subjects.

BRIEF DESCRIPTION OF THE DRAWINGS

The subject matter regarded as the invention is particularly pointed out and distinctly claimed in the concluding portion of this specification. The invention, however, both as to organization and method of operation, together with objects, features, and advantages thereof, may best be understood by reference to the following detailed descriptions when read with the accompanying drawings in which:

Figures 1A, 1B:
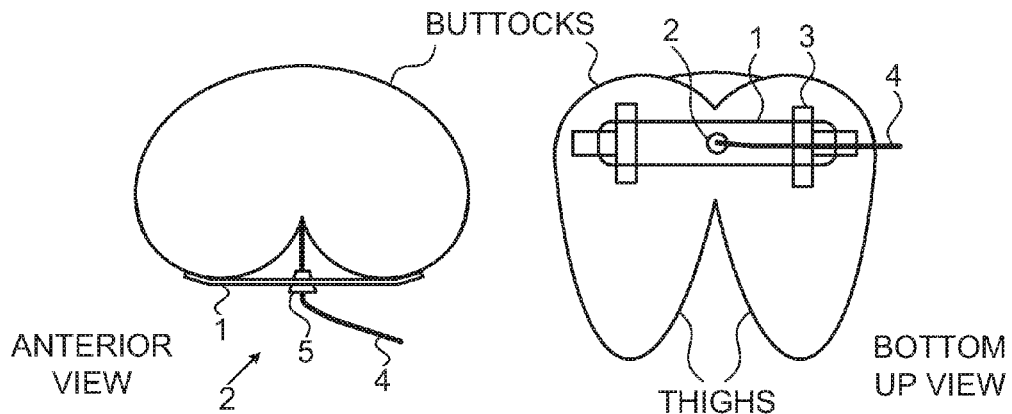
FIGS. 1A and 1B are anterior and bottom-up view illustrations of a bracket assembly of a first embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those of ordinary skill in the art that the present invention may be practiced without these specific details. In other instances, well-known methods, procedures and components have not been described in detail so as not to obscure the present invention.

FIGS. 1A and 1B depict a representative use scenario for a first embodiment of the current invention. In the first embodiment of the present invention, as illustrated in an anterior view in FIG. 1A and a bottom-up view in FIG. 1B, a rigid or semi-rigid bracket 1 spans the width of the buttocks. A catheter fixation element 2 holds the catheter in place—both radially and axially—relative to bracket 1, while bracket 1 is held in place relative to patient anatomy via a suitable adhesive 3 (e.g., adhesive strips). As depicted in FIGS. 1A and 1B, bracket 1 is positioned centrally over the anal verge and secured in place by a suitable adhesive 3, such as, for example, a peel away adhesive or tape that is suitable for use on the body skin and is of appropriate adhesive strength (i.e., not too difficult or too easy to remove) and flexibility. Adhesive 3 helps secure bracket 1 to the buttocks.

The length of bracket 1 may rest between the commode seat and the patient's buttocks, thereby stabilizing bracket 1. Then, a catheter probe 4 is threaded through a central opening or hole 5 in bracket 1, inserted an appropriate depth into the patient, and, then, fastened to bracket 1 via the catheter fixation element 2. Bracket 1 may be manufactured from a material such as hard plastic or metal that is durable and remains rigid under the body weight of a subject.

Advantages of this first embodiment include its manufacture simplicity and ability to provide a strong structure that securely holds catheter probe 4 in place, proximate to the buttocks.

A second embodiment of the present invention is shown in FIGS. 2A-2D. In this embodiment, a device that is in the shape of a full wedge 7 is fastened at (e.g., to both sides of) the interglutial cleft via a suitable adhesive 3.

Figure 2A:
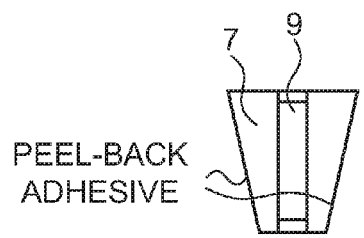
FIG. 2A is an illustration of a front view of a full wedge assembly of a second embodiment of the present invention.

A wedge, such as wedge 7 shown in a front view of FIG. 2A, may be manufactured from material comprising soft foams or sponge elastomers, or other suitable soft, elastic material. Wedge 7 may be a 'full' wedge, a pyramid shape or a squared cone shape where the side surfaces of the shape/object taper outward from an internal end (shown at 20), i.e., the end closer to the patient's anus, to an external end, i.e., the end farther from the patient's anus, although other similar or suitable shapes may be used. For example, the 'wedge' can be straight-sided with the inward tapering of the anatomy being accommodated through the use of highly compliant material to form wedge 7. Wedge 7 should preferably be configured to be small enough to fit comfortably within the interglutial cleft of a human body, with the base end having the smaller cross-sectional area (end 20) being fit adjacent to the anal verge, as shown in use in FIG. 3A, without it being too large so as to cause discomfort to the patient. In certain embodiments, wedge 7 is approximately 2-10 cm high (i.e., from the internal end 20 of wedge 7 to the external end 22 of wedge 7). Wedge 7 is preferably 3-8 cm high, and, more preferably, 4-6 cm high. In one embodiment, wedge 7 is 5 cm high.

In one embodiment, wedge 7 has two lateral sides that lie adjacent to the patient's skin on either side of the interglutial cleft, a front side 24 and a back side 26. In certain embodiments, wedge 7 is approximately 2-10 cm wide (i.e., from one lateral side to another lateral side, 'bridging' the interglutial cleft), and preferably 3-8 cm wide, and more preferably 4-6 cm wide. In one embodiment, wedge 7 is 4 cm wide. In certain embodiments, wedge 7 is approximately 2-10 cm deep (i.e., the front side closer to the front of the patient to the back side closer to the back of the patient), and preferably 3-8 cm deep, and more preferably 4-6 cm deep. In one embodiment, wedge 7 is 4 cm deep.

In one embodiment, each side of wedge 7 is manufactured to have the same angle. In one embodiment, each side of wedge 7 has an angle of (between) approximately 0-45 degrees, and preferably between 5 degrees and 30 degrees, and more preferably between 10 degrees and 20 degrees, with respect to a vertical line from one end to another (i.e., with respect to a longitudinal axis 28 of the wedge). In one embodiment, each side of wedge 7 has an angle of 15 degrees.

In another embodiment, wedge 7 may incorporate or have two different angles on its sides. Specifically, in order to accommodate anatomical/morphological variations in patients, wedge 7 may be formed with sides that are not equally angled, e.g., sides that are angled to match (suited for) the morphological angles of a specific patient. In addition, the side of wedge 7 that attaches to the buttocks may be pulled somewhat by catheter probe 4, and it may be desirable to make the sides of wedge 7 not equally angled so as to avoid discomfort to the patient.

In another embodiment of the present invention, each side of wedge 7 may have different angles such as, for example, four different angles depending on the needs or anatomy of the patient. In yet another embodiment of the present invention, wedge 7 may have multiple sides manufactured at the same angle, and multiple sides manufactured at different angles such as, for example, two sides having a first angle and two different sides having a second, different, angle. In another embodiment, three sides of wedge 7 may have the same angle, while the fourth side has a second, different, angle.

Wedge 7 may be made of, for example, a soft compliant material that accommodates for differences in patient anatomy/morphology and patient movement (for example, changing width of interglutial cleft) during the clinical procedure.

Figure 2B:
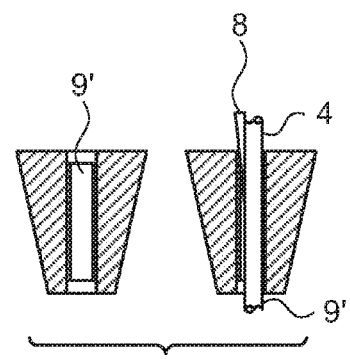
FIG. 2B is an illustration of front cross-sectional views of a full wedge assembly, with and without the catheter probe, of a second embodiment of the present invention.
Figure 2D:
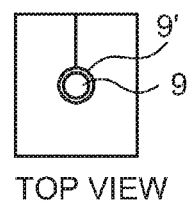
FIG. 2D is an illustration of a top view of a full wedge assembly of a second embodiment of the present invention.
Figure 3A:
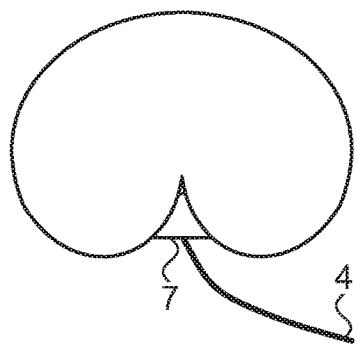
FIGS. 3A and 3B are illustrations of a full wedge assembly and catheter probe of a second embodiment of the present invention as fastened to the buttocks.

In certain embodiments of the present invention, as shown in a cross-sectional front view in FIG. 2A, a channel 9 is formed through the center of wedge 7 from the wide end to the narrow end, and a semi-stiff or stiff tube 9' is threaded through channel 9 so as to keep channel 9 open and to accommodate catheter probe 4. FIG. 2D shows a top view of wedge 7 with channel 9 formed therethrough and tube 9' threaded through/into channel 9. As shown in FIGS. 3A (anterior view) and 3B (bottom up view), catheter probe 4 is fastened to wedge 7 by being inserted or threaded through tube 9'. Catheter probe 4 may be attached to wedge 7 before wedge 7 is attached to both sides of the interglutial cleft.

Catheter probe 4 may be fastened to wedge 7. For example, in addition to stiff or semi-stiff inner member or tube 9', an additional element may be used to affix catheter probe 4 within/to wedge 7. For example, a tapered lock piece 8 (i.e., wedge), as shown in FIG. 2B, may support or secure catheter probe 4 within/to tube 9' in such a way as to allow for fastening of catheter probe 4 to wedge 7 and minimizing the movement of catheter probe 4 relative to wedge 7. Catheter probe 4 may be fastened to wedge 7 by any suitable means, such as, for example, by a belt-like elastic band, a clamp-like structure, a lock piece such as, for example, tapered lock piece 8 or a plastic or rubber stopper-type mechanism. Other fastening means are possible.

Figure 2C:
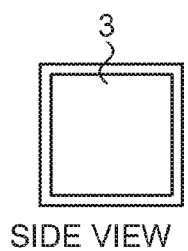
FIG. 2C is an illustration of a side view of a full wedge assembly of a second embodiment of the present invention.
Figure 3B:
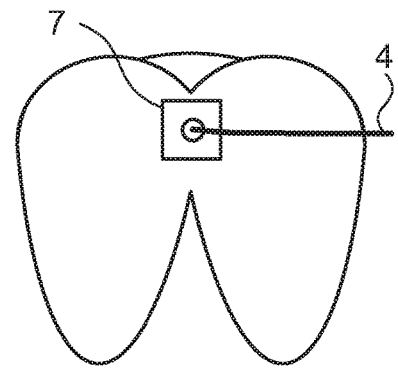

Wedge 7 may be provided with a suitable adhesive 3, for example, on opposing sides of wedge 7, as shown in a side view in FIG. 2C, to allow wedge 7 to be fastened to the buttock(s), i.e., to both sides of the interglutial cleft. In one embodiment, wedge 7 may be fastened to the body in such a way that the side of wedge 7 adjacent to the anal verge is generally directed toward the center of the anal verge, as shown in a posterior view in FIG. 3A and in a bottom up view in FIG. 3B.

Fastening of wedge 7 to the buttock(s) and fastening of catheter probe 4 to the wedge 7 can be done in any order. However, a preferred order of fastening is to first fasten wedge 7 to the body such that the central opening is directed toward the anal verge, and catheter probe 4 is then fixed to the wedge 7 by being inserted or threaded through tube 9' such that it passes through the anus at the proper axial position. Catheter probe 4 may be fastened to wedge 7 through tube 9' by the tapered lock piece 8 or other suitable means for immobilizing catheter probe 4 within wedge 7, as shown in FIG. 2B. Advantages of the second embodiment include ease of use and low production/manufacturing costs.

Figure 4A:
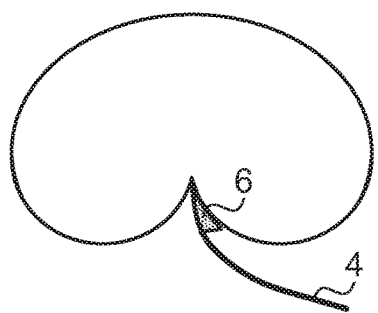
FIGS. 4A, 4B and 4C are illustrations of embodiments of a half wedge assembly of a third embodiment of the present invention.

A third embodiment of the present invention is shown in FIGS. 4A (anterior view) and 4B (bottom-up view). In this embodiment, a device that is in the shape of a half wedge shape 6 is fastened to one buttock on one side of the interglutial cleft by using a suitable adhesive 3, such as a peel away adhesive tape. Half wedge 6 may also be fastened to other suitable positions of the buttocks.

In certain embodiments, half wedge 6 may have the shape of a full wedge 7 that has been split from one end to the other, such that three side surfaces of the half wedge shape taper outward from a base end to an upper end, and the remaining side surface is non-tapered, i.e., is substantially perpendicular with respect to the base and upper surfaces. In certain other embodiments, the shape of half wedge 6 may be unrelated to (dissimilar to) the shape of the shape of wedge 7. In one embodiment, half wedge 6 has an internal end, an external end, a front side and a back side, a lateral side that lies against the patient's skin on one side of the interglutial cleft and an opposing lateral side that does not lie against the patient's skin. In certain embodiments, due to the angling of half wedge 6, the internal end thereof has a comparatively much smaller surface area than that of the external end.

The catheter probe 4 is fastened to the half wedge 6 by a suitable means for attachment, such as, for example tape or a plastic holding device configured on half wedge 6. Optionally, half-wedge 6 has a channel or groove formed into the surface of the lateral side of half-wedge 6 that does not lie adjacent to the patient's skin, in order to support the position of the probe.

Half wedge 6 may be configured with different angles on the side of half wedge 6 that guides catheter probe 4 towards the anal cavity relative to the side of the half wedge 6 that attaches to the buttock. For example, FIGS. 4A and 4C show anterior views of half wedge 6 having different angles, wherein half wedge 6' depicted in FIG. 4C has a steep-side, namely a lateral side that lies against the patient's skin that is more widely angled outward than is the corresponding side of half wedge 6 depicted in FIG. 4A. Thus, FIG. 4C shows half wedge assembly 6' that is steeper-sided than half wedge assembly shown in FIG. 4A. Half wedge 6' in FIG. 4C can also be regarded as the half wedge 6 of FIG. 4A rotated. The steeper-sided wedge shown in FIG. 4C may be used, for example, for buttocks with a relatively shallow cleft. In this way, half wedge 6 may accommodate for anatomical/morphological variations in patients.

In one embodiment, as shown in FIG. 4A, the angle of the lateral side of half wedge 6 that guides catheter probe 4 towards the anal cavity with respect to the lateral side that lies against the patient's skin is configured to have an angle of approximately 5-40 degrees, preferably 10-30 degrees and more preferably 15-25 degrees. In one embodiment, the angle of the lateral side of half wedge 6 that guides catheter probe 4 towards the anal cavity with respect to the lateral side that lies against the patient's skin is configured to have an angle of 20 degrees.

In another embodiment, as shown in FIG. 4C, the angle of the lateral side of half wedge 6 that guides catheter probe 4 towards the anal cavity with respect to the lateral side that lies against the patient's skin is configured to have an angle of approximately 30-60 degrees, preferably 35-55 degrees, and more preferably 40-50 degrees. In one embodiment, the angle of the lateral side of half wedge 6 that guides catheter probe 4 towards the anal cavity with respect to the lateral side that lies against the patient's skin is configured to have an angle of 45 degrees.

Figure 4B:
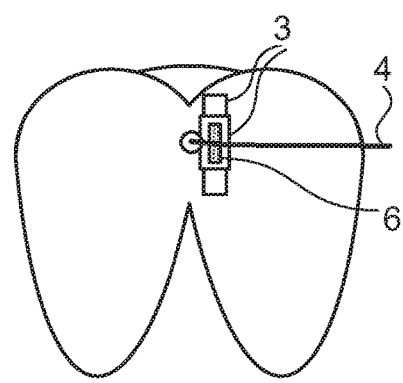
Figure 4C:
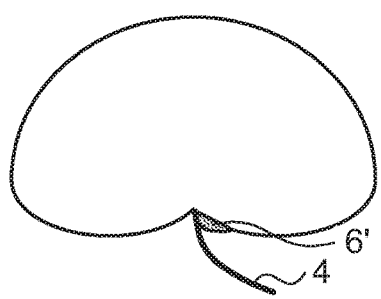

FIG. 4B shows a bottom up view of the half wedge 6 and catheter probe 4 fastened to one side of the interglutial cleft of a patient. Fastening of the half wedge 6 to the buttock and the fastening of catheter probe 4 to the half wedge 6 can be performed in any order. However, a preferred order of fastening is to first fasten the half wedge 6 to the buttock in such a way that the side of the half wedge 6 adjacent to the anal verge is generally directed toward the anal verge and slightly to one side (preferably, the side that half wedge 6 is on). Then, catheter probe 4 is affixed to the half wedge 6 such that it passes, by being pushed, through the anus verge and is at the proper axial position/depth.

Half wedge 6 may be manufactured from a material that is durable, such as hard plastic or metal, or from a more compliant material comprising semi-rigid and soft foams or sponge elastomers, or other suitable soft, elastic material.

Half wedge 6 should preferably be small enough to fit comfortably within the interglutial cleft of a human body, with the base end having the smaller cross-sectional area being fit adjacent to the anal verge, as shown in FIG. 4A, without being too large so as to cause discomfort to the patient. In certain embodiments, half wedge 6 is approximately 1-10 cm high, preferably 2-8 cm high, and more preferably 3-5 cm high. In one embodiment, the height of half wedge 6 is 4 cm.

In certain embodiments, half wedge 6 is 0.5-5 cm wide, preferably 1-4 cm wide, and more preferably 1-3 cm wide. In one embodiment, half wedge 6 is 2 cm wide. In certain embodiments, half wedge 6 is approximately 0.5-5 cm deep (i.e., the front side closer to the front of the patient to the back side closer to the back of the patient), preferably 1-4 cm deep, and more preferably 1-3 cm deep. In one embodiment, half wedge 6 is 2 cm deep.

Advantages of this third embodiment include its simplicity, relatively unobstructed opening for stools to pass, low production/manufacturing costs, freedom of anatomical movement of the patient, and in situ proximity to skeletal support (ischial tuberosity) to minimize movement of catheter probe 4 in the axial direction relative to the anus.

Figure 5:
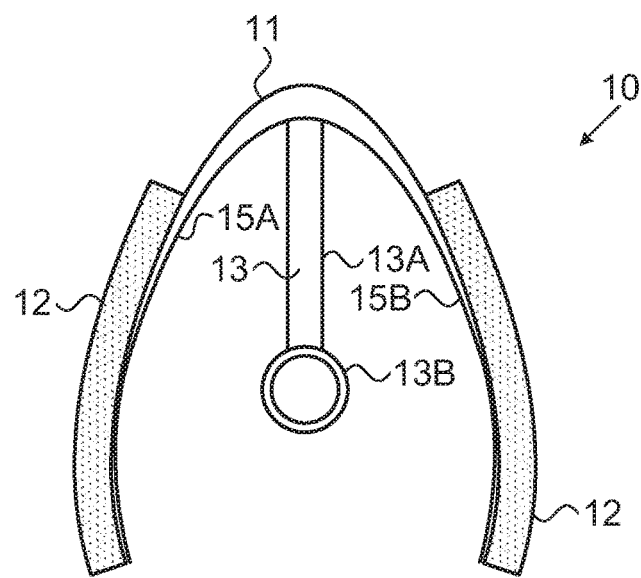
FIG. 5 is an illustration of a top view of a two-sided leaf spring assembly of a fourth embodiment of the present invention.
Figure 6A:
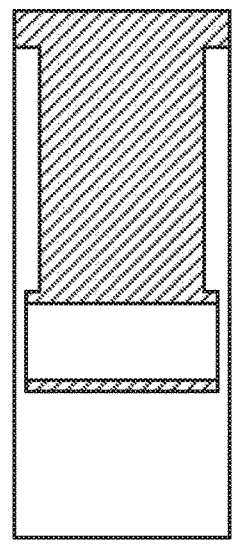
FIGS. 6A and 6B are cross-sectional illustrations of a two-sided leaf spring assembly of a fourth embodiment of the present invention.
Figure 6B:
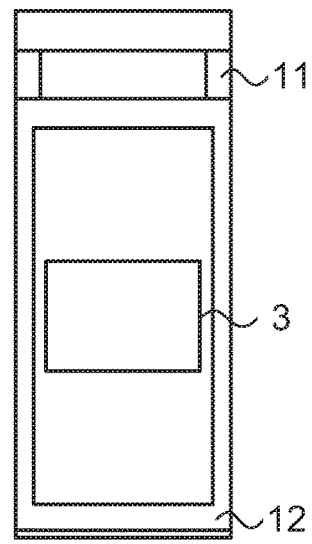

A fourth embodiment of the present invention is shown in FIGS. 5, 6A and 6B. In this embodiment, a two-sided leaf spring assembly 10 allows for changes or variations in interglutial cleft geometry, while also providing a surface which is attachable to the patient's body and for maintaining a secure positioning of catheter probe 4.

In certain embodiments of the present invention, as illustrated in top view in FIG. 5, leaf spring assembly 10 comprises a spring-like semi-rigid leaf spring housing 11 that acts as the two-sided leaf spring. Semi-rigid housing 11 may be manufactured from plastic or other suitable (e.g., flexible) material that allows for, or imparts it, a semi-rigid flexibility. In general, leaf spring assembly 10 and semi-rigid leaf spring housing 11 comprises two arms, (e.g., arms 15a and 15b) that may form an object that resembles or has a "U" shape, "V" shape, "C" shape or horseshoe shape, although other shapes may be used. For example, leaf spring assembly 10 and semi-rigid leaf spring housing 11 may form a circular, oval, or elliptical shape, wherein the arms of semi-rigid leaf spring housing 11 are connected to each other at/by their ends or are at least closer to each other than is depicted in FIG. 5. The leaf spring assembly and the semi-rigid leaf spring housing may have any shape that imparts them the functionality described herein, and all such shapes, whether mentioned herein or not, are collectively referred to herein as "open shaped leaf spring assemblies". Alternatively, the leaf spring assembly may be a closed object having, for example, a flattened (e.g., generally oval-shaped) shape that facilitates insertion thereof into the interglutial cleft of a subject and allows for natural sitting position during the procedure. The closed shaped leaf spring assembly may generally resemble the shape of leaf spring assembly 10, except that in the closed shaped leaf spring assembly there is no open end.

In certain embodiments of the present invention a width 14 of leaf spring housing 11 is defined as the dimension of leaf spring housing 11 spanning arms 15a and 15b (e.g. the width of leaf spring housing 11 bridges the interglutial cleft when the device is fastened to the buttocks of the patient). In certain embodiments, the height of leaf spring housing 11 is defined as the dimension of leaf spring housing 11 perpendicular to the width at/of the apex (i.e. the curved portion, or connecting 'area', connecting arms 15a and 15b) of the "U"-shaped leaf spring housing 11. In certain embodiments, leaf spring housing 11 is approximately 1-5 cm high, preferably 1-4 cm high, and more preferably 2-4 cm high. In one embodiment, leaf spring assembly 11 is 3 cm high. In certain embodiments of the present invention, leaf spring housing 11, when in a resting position, i.e., it is not yet installed, is approximately 1-7 cm wide, preferably 2-6 cm wide, and more preferably 3-5 cm wide. In one embodiment, leaf spring housing 11 is 4 cm wide. It is noted, however, that the compliance (i.e. flexibility) of the housing may change the overall width of leaf spring housing 11 once it has been fastened to the buttocks of the patient due to compression thereof. In other words, leaf spring housing 11 may have a 'free' width or 'released' position, or 'decompressed' width, or expanded width, which is the width, or position, or state of device 11 when no external force is applied to it (such as when the device is not installed on a subject; e.g., when the device resides in a package), and a 'compressed' width, which is the device's width when the device is installed on a subject. The ability of the width (14) of leaf spring housing 11 to forcedly (i.e., under pressure) change, or flex, from the free width to the compressed width enable the spring-like arms 15A and 15B to be in compressive/tight contact with the subject while providing an opening suitable for the passage of stools.

In certain embodiments of the invention, arms 15a and 15b are approximately 1-6 cm long, preferably 2-5 cm long, and more preferably 3-4 cm long. In one embodiment, arms 15a and 15b are 3.5 cm long. In one embodiment the length of arms 15a and 15b from the apex of leaf spring housing 11 is approximately 5 cm, although it is noted that other lengths are possible depending on the length of arms 15a and 15b. In some embodiments, the lengths of arms 15a and 15b are substantially identical, although in other embodiments this need not be so (i.e., their lengths may differ).

As may be seen in FIG. 5, a soft foam strip 12 may be added to the leaf spring housing 11 in order to improve conformity of the leaf spring assembly 10 to the patient attachment area. As shown in FIG. 5, soft foam strips 12 are configured on or attached to the exterior portion/surface of arms 15a and 15b of the two-sided leaf spring housing 11 where the leaf spring assembly 10 would otherwise contact the surface of the buttocks. However, it is noted that soft foam strips 12 may be placed anywhere on leaf spring assembly 10 in order to accommodate for different patient morphologies without impairing or detracting from patient comfort. Soft foam strips 12 generally increase the region in intimate contact between device and patient so as to promote, or sustain, both adhesion and patient comfort.

In this embodiment, there are two main functional elements on leaf spring assembly 10. The first functional element is the two-armed housing 11, which is designed or configured to maintain positive contact pressure between the attachment surface on the patient's buttocks while also conforming to changes in anatomical and physiological opening variations of individual patients. This is accomplished by using a relatively "soft" spring constant with large free spacing of the opening between the two "arms" 15a and 15b.

Figure 8:
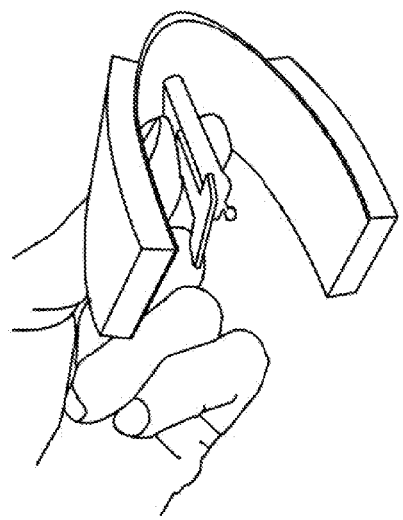
FIG. 8 is an illustration of a series of steps for attaching the probe to a probe support arm of one embodiment of the present invention.
Figure 8:
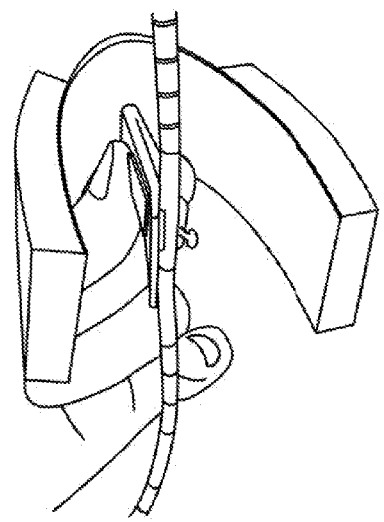
Figure 8:
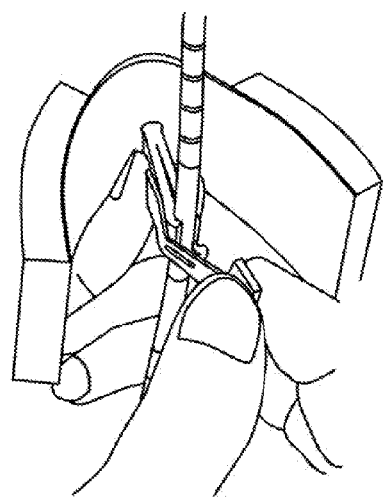

The second functional element of the leaf spring assembly 10 is a probe support 13, which is configured to hold probe 4 securely in a set, or fixed, position relative to leaf spring assembly 10. Probe support 13 has a retaining piece/element 13B, which may be in the form of a ring or a semicircle/half/partial ring (e.g., C-shaped clam, gripper or clasp), or other probe attachment element, which is attached at the (distal) end of a support or connecting arm 13A. Probe support arm 13A may be connected to housing 11, extend in-between two arms 15a and 15b and configured to accept a catheter probe for performing the anorectal diagnostic procedure. Support (or connecting) arm 13A is attached to leaf spring assembly 10 in such a way that it is rigid relative to housing 11 (i.e., connection point) of arms 15a and 15b and provides for (enables, or can be used for) attachment and removal of catheter probe 4. As shown in FIG. 5, probe support arm 13A may be configured on (connected to) the base (i.e., connection point) of leaf spring assembly 10, or it may otherwise be generally connected to leaf spring assembly 10 in a way that allows arms 15a and 15b of leaf spring assembly 10 and semi-rigid leaf spring housing 11 to flex, e.g., in response to physiological changes in interglutial spacing, without appreciably moving the position of probe support arm 13A, and hence probe 4, relative to the anal verge. FIG. 5 shows a retaining piece 13B for holding probe 4, which is in the form of a ring, and FIG. 8 shows a retaining piece 13B which is in the form of a C-shaped clamp or gripper element.

Figure 7A:
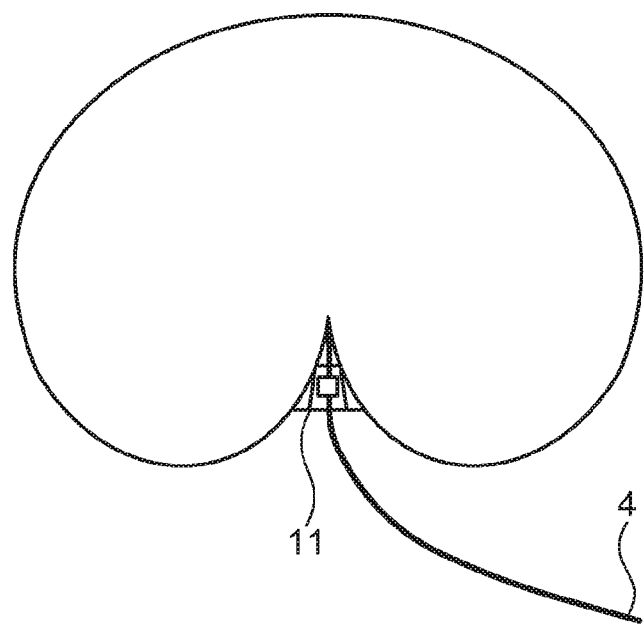
FIGS. 7A and 7B are illustrations of the two-sided leaf spring assembly of a fourth embodiment as fastened to the buttocks.
Figure 7B:
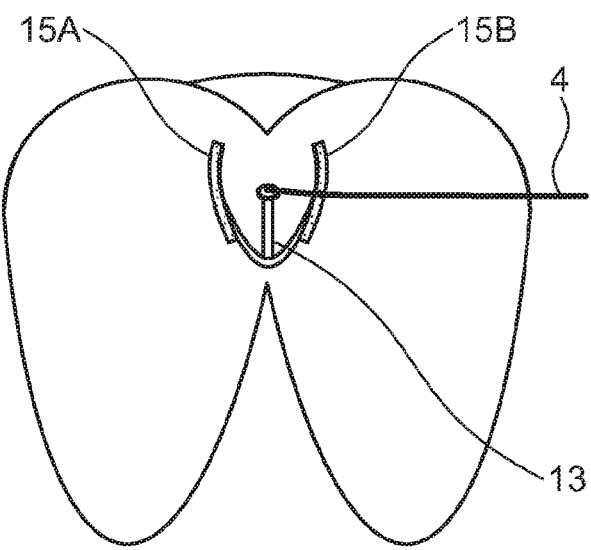

Fastening of leaf spring assembly 10 to the buttock(s) and attachment of catheter probe 4 to leaf spring assembly 10 may be carried out in any order. However, in a preferred order, leaf spring assembly 10 is first fastened to the body. In certain embodiments of the present invention, the outer surfaces of arms 15a and 15b of leaf spring housing 11 (including the foam strips 12) are fastened to the sides of the buttocks using contact adhesive, such as, for example, a suitable adhesive 3, as shown in an anterior view in FIG. 7A and in a bottom-up view in FIG. 7B. Adhesive 3 may be or include a double-sided bonding tape, with one side permanently adhesively attached to each of the spring arms (15A,15B) or foam strips (12), and the other side having an (external) adhesive layer protected by a removable paper which, when removed, exposes the adhesive layer by which leaf spring assembly 10 can securely (e.g., hold on for the duration of a procedure), yet removably (e.g., when desired), be adhered to a subject at the designated location. In certain embodiments of the present invention it may be advantageous to position the leaf spring assembly 10 as close to the anal verge as possible to maximize or optimize structural support (e.g., via proximity to the skeletal structure at the ischial tuberosity). The two-side spring arms (or 'wings') of the leaf spring assembly 10 may, at times, get detached from the person. In order to avoid that problem, a more flexible and softer materials (e.g., plastic) may be used (e.g., a material having a relatively low durometer number may be used). For example, a material called teslin, which is very flexible, yet sturdy, may readily conform to the configuration of the glutei. The plastic material of the spring arms may be more thick, or thickest, at the bending area. However, making it thinner, or thin enough, at the bending area may make the leaf spring assembly more flexible. Since the leaf spring assembly may be a one-time device (i.e., used one time), the bending area is not required to withstand many stressors.

In the preferred order, catheter probe 4 is then fixed or fastened to probe support 13 of leaf spring housing 11 by attaching it to retaining piece 13B, e.g., by being threaded or inserted through a ring or clamped by a C-shaped clamp or gripper element or other attachment feature, in such a way that catheter probe 4 is directed toward the anal verge, such that it passes, e.g., by being pushed, through the anus and is at the proper axial/depth position. Catheter probe 4 may be fastened to the probe support 13 by any suitable means, such as, for example, a belt-like elastic band, a clamp-like structure, a lock piece such, for example, tapered lock piece 8, a plastic or rubber stopper-type mechanism, or any other suitable fastening means.

A person having ordinary skill in the art will appreciate that there are many different ways in which catheter probe 4 may be fastened to retaining piece 13B of probe support 13 of leaf spring housing 11. For example, FIG. 8 is a step-wise depiction of an embodiment of the present invention wherein catheter probe 4 is fastened to retaining piece 13B of probe support 13 of the leaf spring housing 11 in a clamp-like structure, rather than a ring, using an elastic belt-like band. As shown in FIG. 8, first (at STEP 1) the leaf spring housing 11 is held securely, e.g., by probe support an 13A, and then (at STEP 2) catheter probe 4 is pushed sideways through a side opening of a clamp-like retaining element 13B structure formed by a split in probe support 13. An elastic belt-like band is then (at STEP 3) pulled from its attachment site on one side of probe support 13 to the opposite side and secured in place. As depicted in FIG. 8, at STEP 4 the elastic belt-like band is secured across the opening of the clamp-like structure by positioning a slit formed in the middle of the belt-like band over and onto a knob formed as part of probe support 13.

Thus, with respect to leaf spring assembly 10, three design goals are addressed herein: 1) patient freedom of movement is minimally affected; 2) catheter probe 4 is secured and maintained centrally to and directed toward the anal verge; and 3) a maximal opening is provided to allow for passage of stools or waste material. Advantages of the invention include simplicity of design, largely unobstructed opening for passage of stools, low production/manufacturing costs, freedom of anatomical movement, and in situ proximity to skeletal support (ischial tuberosity) to minimize movement of catheter probe 4 relative to the anus.

It may sometimes be difficult to adjust a band (e.g., the belt-like elastic band mentioned above) and, considering the sensitivity of the region of the anus verge, manipulation of the band at that region should be minimized to minimize discomfort. It may sometimes be difficult to adjust the clasp, or clamp, and reposition the probe particularly when the patient is seated on the commode. Such difficulties, or concerns, may be mitigated by configuring the catheter/probe fixation device such that it is self-contained in/between two semicircular (half), adjustable, rings that encircle and centralize the probe. The two adjustable semicircular rings may be configured to function as a clamp.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall with the true spirit of the invention.

The invention claimed is:

1. An anal fixation device for use in anorectal diagnostic procedures, comprising:
   a housing configured to accept a probe and to maintain the probe in a fixed position relative to the subject's anus verge during an anorectal diagnostic procedure, said housing comprising two arms and a base which is a connection point of the two arms; and
   a probe support comprising a support arm and a retaining piece, wherein:
      a proximal end of said support arm is connected to the base such that the two arms can flex without moving said support arm,
      said support arm extending in-between the two arms,
      the retaining piece is connected to a distal end of said support arm, and
      the retaining piece is configured to accept the probe for performing anorectal diagnostic procedure.

2. The anal fixation device according to claim 1, wherein the two arms of said housing are configured to span the interglutial cleft of a subject.

3. The device according to claim 1, wherein the housing has a first, uncompressed width in an uninstalled configuration, and has a second, compressed width in an installed configuration.

4. The device according to claim 1, wherein the two arms oppose each other and are positioned to create an open space therebetween, wherein said support arm extends into said open space.

5. The anal fixation device according to claim 1, wherein the housing includes a plastic material.

6. The anal fixation device according to claim 1, wherein the housing is configured to be fastened at the interglutial cleft of the subject.

7. The anal fixation device according to claim 1, wherein the two arms form an open object or a closed object.

8. The anal affixation device according to claim 1, wherein the probe support comprises a means for fastening or retaining the probe.

9. The device according to claim 8, wherein the fastening means is selected from the group consisting of a belt-like elastic band, a clamp-like structure, a lock piece, a plastic or rubber stopper-type mechanism and a tapered lock piece.

10. The anal fixation device according to claim 8, wherein the fastening means comprises a belt-like elastic band attached to one side of said probe support.

11. The anal fixation device according to claim 10, wherein said probe support has a said clamp-like structure with a side opening capable of receiving the probe.

12. The anal fixation device according to claim 11, wherein the belt-like elastic band is configured to be secured across the side opening of said clamp-like structure to thereby secure the probe, by positioning a slit formed in the middle of the belt-like elastic band over and onto a knob formed as part of said probe support.

13. The anal affixation device according to claim 1, wherein the housing comprises a semi-rigid plastic material.

14. The anal fixation device according to claim 1, wherein said housing has a width defined as a dimension of the housing spanning the two arms, and a height that is defined as a dimension of the housing perpendicular to a width of said housing at an apex of the two arms, wherein said support arm extends between said arms approximately half of the length of the height of said housing.

15. An anal fixation device for use in anorectal diagnostic procedures, comprising:

a housing comprising two arms and a base, wherein: the two arms form a shape selected from a group consisting of open shape and closed shape, the base is a connection point of the two arms, and said housing is configured to span the interglutial cleft of a subject; and a probe support comprising a support arm and a retaining piece, wherein:

a proximal end of said support arm is connected to the base such that the two arms can flex without moving said support arm, the support arm extending in-between the two arms, the retaining piece is connected to a distal end of said support arm, and the retaining piece configured to accept and retain a probe for performing an anorectal diagnostic procedure.

16. The anal fixation device according to claim 15, wherein the housing comprises a semi-rigid plastic material.

17. The anal fixation device according to claim 15, wherein the probe support further comprises a fastening means for fastening and retaining the probe, said fastening means is selected from the group consisting of a belt-like elastic band, a clamp-like structure, a lock piece, a plastic or rubber stopper-type mechanism and a tapered lock piece.

18. The anal fixation device according to claim 15, wherein each arm comprises a foam strip having an adhesive material configured to be adhered to the subject's buttocks.

19. The anal fixation device according to claim 18, wherein said foam strip is located on an external surface of said two arms.

20. The anal fixation device according to claim 15, wherein the housing has a first, uncompressed width in an uninstalled configuration, and has a second, compressed width in an installed configuration.

21. The anal fixation device according to claim 15, wherein the two arms oppose each other and are positioned to create an open space therebetween, wherein said support arm extends into said open space.

22. The anal fixation device according to claim 15, wherein the housing includes a plastic material.

* * * * *